(12) United States Patent
Pellegrino

(10) Patent No.: US 10,610,481 B1
(45) Date of Patent: Apr. 7, 2020

(54) COMPOSITION FOR ORAL AND DENTAL CARE AND CLEANING

(71) Applicant: Ingrid Cristina Pellegrino, Provincia de Santa Cruz (AR)

(72) Inventor: Ingrid Cristina Pellegrino, Provincia de Santa Cruz (AR)

( * ) Notice: Subject to any disclaimer, the term of this patent is extended or adjusted under 35 U.S.C. 154(b) by 0 days.

(21) Appl. No.: 16/429,385

(22) Filed: Jun. 3, 2019

(51) Int. Cl.
| | | |
|---|---|---|
| *A61K 8/9794* | (2017.01) | |
| *A61K 8/34* | (2006.01) | |
| *A61K 8/73* | (2006.01) | |
| *A61K 8/55* | (2006.01) | |
| *A61K 8/41* | (2006.01) | |
| *A61K 8/60* | (2006.01) | |
| *A61K 8/49* | (2006.01) | |
| *A61K 8/58* | (2006.01) | |
| *A61K 8/37* | (2006.01) | |
| *A61K 8/368* | (2006.01) | |
| *A61Q 11/00* | (2006.01) | |
| *A61K 8/36* | (2006.01) | |

(52) U.S. Cl.
CPC ............ *A61K 8/9794* (2017.08); *A61K 8/342* (2013.01); *A61K 8/345* (2013.01); *A61K 8/36* (2013.01); *A61K 8/368* (2013.01); *A61K 8/37* (2013.01); *A61K 8/41* (2013.01); *A61K 8/4946* (2013.01); *A61K 8/553* (2013.01); *A61K 8/58* (2013.01); *A61K 8/60* (2013.01); *A61K 8/73* (2013.01); *A61Q 11/00* (2013.01); *A61K 2800/51* (2013.01)

(58) Field of Classification Search
None
See application file for complete search history.

(56) References Cited

U.S. PATENT DOCUMENTS 10,149,815 B2   11/2018   Price

*Primary Examiner* — Nannette Holloman
(74) *Attorney, Agent, or Firm* — King & Schickli, PLLC

(57) ABSTRACT

A composition for oral and dental care and cleaning, preferably, a concentrated composition that remains stable during long shelf-life and that accentuates the useful properties of coconut oil for obtaining a product which has antibacterial properties, facilitates the removal of bacterial plaque and delays its appearance on the surface of the teeth, whitens teeth, and freshens breath.

Figures 1, 2, 3, 4:
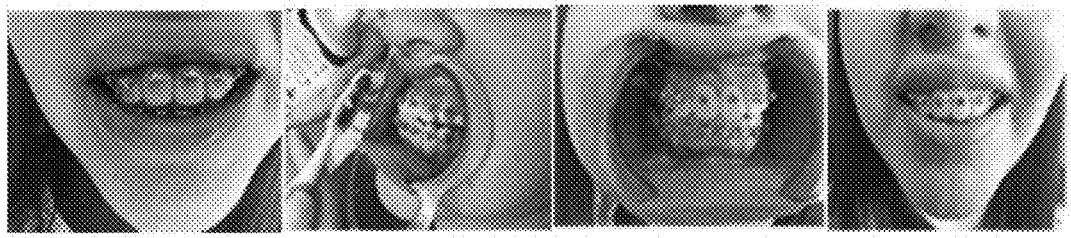

18 Claims, 7 Drawing Sheets
(7 of 7 Drawing Sheet(s) Filed in Color)

COMPOSITION FOR ORAL AND DENTAL CARE AND CLEANING

The disclosure of U.S. Provisional Patent Application 62/686,723 is incorporated herein by reference.

The patent or application file contains at least one drawing executed in color. Copies of this patent or patent application publication with color drawing(s) will be provided by the Office upon request and payment of the necessary fee.

FIELD OF THE INVENTION

This disclosure is concerned with compositions for oral care and cleaning containing coconut oil and having cosmetic properties and properties for the prevention of mouth and teeth diseases.

BACKGROUND

Coconut oil is an edible oil extracted from the kernel or meat of mature coconuts harvested from the coconut palm (*Cocos nucifera*). Because of its high saturated fat content, it is slow to oxidize and, thus, resistant to rancidification.

Coconut oil is comprised mainly of saturated fat (82% of total). Half of the saturated fat content of coconut oil is lauric acid, while other significant saturated fats are myristoleic acid and palmitoleic acid. Monounsaturated fats comprise 6% of total fats, and polyunsaturated fats comprise 2%. Additionally, coconut oil contains phytosterols.

Coconut oil has always been used for nutritional and therapeutic purposes due to its properties and health benefits. In addition, it is used as a natural beauty product and a skin and hair care product. Moreover, among its most important uses are the regulation of metabolism and weight for weight loss and the strengthening the immune system.

One of the components of coconut oil is lauric acid, which offers many health benefits, such as the benefit of eliminating pathogenic bacteria, fungi and some viruses, among others. Other components are antioxidant phenolic acids, which contain protective properties against free radicals and cardiovascular diseases.

Within the food industry, some studies indicate that the use of coconut oil has contributed to health care in general, but especially in the treatment and reduction of cholesterol, the reduction of cardiac distress, the improvement of digestive processes and positive results in the treatment of infectious diseases.

In cosmetic use, coconut oil has proven positive results preventing skin aging, moisturizing the skin, and helping prevent skin diseases.

Regarding its use in oral care and cleaning, U.S. Pat. No. 9,114,097 (B1) discloses a natural toothpaste composition which promotes the healthy effects of whitening teeth, freshening the breath, sanitizing the mouth, and eliminating bacterial plaque and accumulation of tooth enamel, and which comprises coconut oil in combination with freshening agents, stevia and other ingredients such as antioxidants, flavor enhancers and/or anti-inflammatory agents. The composition for oral care in accordance with one embodiment includes about 10% to 45% by weight of coconut oil as an antibacterial and tooth whitening agent. In another embodiment, the composition further comprises baking soda as an abrasive, which may aid in removing bacterial plaque from the surface of the teeth; besides, it includes stevia as antioxidant, gingival anti-inflammatory and flavor enhancers, glycerin, such as vegetable glycerin, as moisturizing agent, and it may also include an additional natural flavoring such as peppermint extract.

U.S. Ser. No. 10/149,815 (B2), the disclosure of which is incorporated herein by reference, discloses formulations for oral care products incorporating coconut oil for effectively removing oral bacteria and methods for making such products. The preferred mouth rinse contains alkaline water, coconut flavor oil extract, sodium lauryl sarcosinate, zinc chloride, 30% xylitol solution, glycerin, Aloe Barbadensis leaf juice and, optionally, sodium benzoate, de-ionized water and mint flavor extract. A preferred formulation of toothpaste contains alkaline water, coconut oil, hydrated sylica sident 9, hydrated sylica sident 22s, glycerin, xylitol, Irish moss, sodium coco sulphate, Aloe Barbadensis leaf juice, titanium dioxide and flavor. The percentage of coconut oil content in the preferred products is in the range of 20% to 80%, but most preferably 40% to 60%.

In a preferred formulation of U.S. Ser. No. 10/149,815, the composition for oral care and cleaning contains 35.5% alkaline water, 27.75% coconut oil, 15.4% hydrated sylica sident 9, 2,8% hydrated sylica sident 22s, 10.5% glycerin, 4% xylitol, 1.4% Irish moss, 0.7% sodium coco sulphate, 0.7% organic Aloe Barbadensis leaf juice, 0.65% titanium dioxide and 0.6% flavor.

Notwithstanding the above, it still remains desirable to provide new oral hygiene products made from naturally occurring products, such as coconut oil, that accentuate its useful antimicrobial and whitening properties for facilitating removal of bacterial plaque, delaying its appearance over a longer period of time compared to conventional toothpaste. Likewise, there is a need for new products that do not comprise harmful ingredients such as sodium lauryl sulfate, a common ingredient in personal hygiene products used as foaming agent but which has been questioned because of its adverse health effects. The Skin Deep Cosmetic Safety Database by Environmental Working Group (EWG) classified this compound as expected to be of "moderate concern" for carcinogenicity, neurotoxicity, organ system toxicity, skin irritation and endocrine disorder.

SUMMARY

One aspect of the disclosure is to provide a coconut oil-based composition for oral and dental care and cleaning, preferably, a concentrated composition that remains stable during long shelf-life and that accentuates the useful properties of coconut oil for obtaining a product which has antibacterial properties, facilitates the removal of bacterial plaque and delays its appearance on the surface of the teeth, whitens teeth, and freshens breath.

Additionally, the composition for oral and dental care and cleaning of the disclosure has the property of facilitating oral mucous restoration due to the healing properties of coconut oil, and it further aids at preventing the appearance of virus, fungi and bacteria due to the antibacterial properties of coconut oil. These beneficial properties allow the composition of the invention to be also used for cosmetic treatment of skin or other human or animal body mucus, as due to its nature the composition entails healing, antibacterial, softening and moisturizing properties that make it compatible with such applications.

As a result of the nature of the composition for oral and dental care and cleaning posed by the present invention, it is possible to use small doses of a single droplet (0.05 ml) for obtaining a quick removal of plaque and fresh breath as well as an immediate clean mouth-feel effect, not being it necessary to wash the mouth after its use because it does not foam as it lacks the foaming agent sodium lauryl sulfate, a conventional ingredient of toothpastes whose use has been questioned.

An additional aspect of the disclosure is to provide a composition for oral and dental care and cleaning, and more particularly, of a toothpaste in the form of a concentrated gel that achieves the healthful benefits mentioned hereinabove and that also comprises natural components or synthetic components with low to none health risk.

In one aspect of the disclosure, a coconut oil-based composition for oral and dental care and cleaning, comprises:
25% to 45% w/w Purified Water q.s.
25% to 35% w/w Coconut oil
20% to 23% w/w First Moisturizing Agent,
7% to 10% w/w Second Moisturizing Agent,
0.3% to 2.5% w/w Structuring Agent,
0.15% to 0.3% w/w Emulsifier/Emollient,
0.1% to 0.3% w/w gel thickener agent,
0.05% to 0.15% w/w chelating agent,
0.02% to 0.05% w/w conditioning agent,
0% to 5% w/w pH-regulating agent,
0% to 5% w/w alkalinizing agent,
0.025% to 0.30% w/w of at least one preservative agent, and optionally, 0.5% to 2.5% of at least one flavoring.

In any disclosed embodiment, the composition may be in the form of a toothpaste or a gel.

BRIEF DESCRIPTION OF THE DRAWING FIGURES

Figures 65, 66:
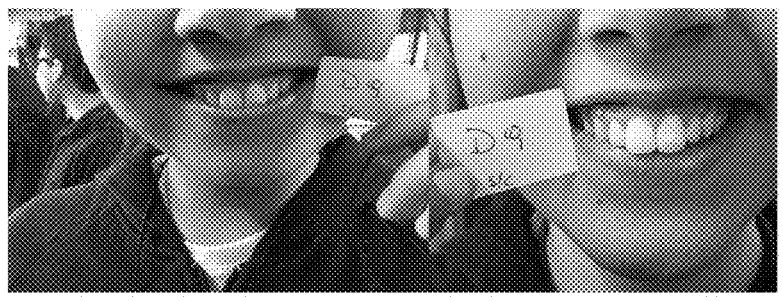

FIGS. 1-66 are photographs illustrating the below-described examples relating to the efficacy of the disclosed composition.

DETAILED DESCRIPTION OF THE INVENTION

Any of all of the foregoing aspects may be achieved by a composition comprising coconut oil as active ingredient deionized water (vehicle), a moisturizing agent such as glycerin and propylene glycol, a structuring agent and emulsifier stabilizer such as Xanthan gum, an emulsifier such as soybean lecithin, an emulsifier, stabilizer or thickener for gel such as a non-ionic polyoxyethylene ether of higher saturated fatty alcohols (cetyl/stearyl alcohol), a chelating agent such as disodium EDTA, a pH-regulating agent and an alkalinizing agent such as TEA (triethanolamine); an acidity regulator such as lactic acid, a conditioning agent, a sweetener such as sucralose, and at least one preservative selected from the group of potassium sorbate, imidazolidinyl urea, propylparaben, methylparaben, sodium benzoate.

This results in the obtention of a composition in the form of a concentrated gel that protect oral health of gums, palate, mucus and tongue.

Additionally, it promotes good dental hygiene contributing to the prevention of diseases by removing and inhibiting bacterial plaque, and it also promotes tooth whitening by means of a formulation with cosmetically and pharmacologically accepted ingredients.

Therefore, the present composition further promotes health and beauty, helping prevent infectious diseases caused by fungi, bacteria or viruses.

Further, the composition regulates oral pH, contributing to the user's health. Food and fluid intake alters the natural pH within the mouth, resulting in an imbalance which causes enamel demineralization, neck caries, gingival retraction, dental myolysis, neck demineralization, and white stains on teeth, among others.

Therefore, the disclosed composition aids in preventing these ailments by regulating the pH in the mouth.

In some embodiments, a composition for oral and dental care and cleaning comprises the ingredients listed hereinbelow, whose quantities are expressed in percentage ranges given by weight:
25% to 45% w/w purified water quantim satis (q.s.)
25% to 35% w/w coconut oil
20% to 23% w/w first moisturizing agent (glycerin)
7% to 10% w/w second moisturizing agent (propylene glycol)
0.3% to 2.5% w/w structuring agent (Xanthan gum)
0.15% to 0.3% w/w emulsifier/emollient (soybean lecithin)
0.1% to 0.3% w/w gel-forming thickener (cetyl alcohol ether and polyethylene glycol)
0.05% to 0.15% w/w chelating agent (disodium EDTA);
0.02% to 0.05% w/w conditioning agent (sucralose);
0% to 5% w/w triethanolamine pH-regulating agent (q.s. pH)
0% to 5% w/w acidity regulator (lactic acid);
0.2% to 0.3% w/w antimicrobial agent (imidazolidinyl urea);
0.05% to 0.15% w/w preservative agent (potassium sorbate);
0.05% to 0.15% w/w preservative agent (methylparaben);
0.05% to 0.15% w/w preservative agent (Sodium Benzoate);
0.025% to 0.05% w/w preservative agent (propylparaben); and
Optionally, 0.5% to 2.5% of at least one flavoring.

Experimental Studies

Two gel compositions of different flavors were prepared:

| | Common name | % w/w |
|---|---|---|
| 1. | Chocolate flavored gel composition for 100 g | |
| | Deionized water | q.s. 100 |
| | Coconut Oil | 30 |
| | Glycerin | 23 |
| | Propylene glycol | 10 |
| | Xanthan gum | 0.6 |
| | Innidazolidinyl urea | 0.3 |
| | Soybean lecithin | 0.25 |
| | Ceteareth 20 | 0.2 |
| | Methylparaben | 0.1 |
| | Disodiunn EDTA | 0.1 |
| | Propylparaben | 0.05 |
| | Potassium sorbate | 0.15 |
| | Sodium benzoate | 0.1 |
| | Lactic acid | 0.73 |
| | Sucralose solution 10% | 0.4 |
| | Chocolate Flavor | 2.0 |
| 2. | Mint flavored gel composition for 100 g | |
| | Deionized water | q.s. 100 |
| | Coconut Oil | 30 |
| | Glycerin | 23 |
| | Propylene glycol | 10 |
| | Xanthan gum | 1.8 |
| | Innidazolidinyl urea | 0.3 |
| | Soybean lecithin | 0.25 |
| | Ceteareth 20 | 0.2 |
| | Methylparaben | 0.1 |
| | Disodiunn EDTA | 0.1 |
| | Propylparaben | 0.05 |

-continued

| Common name | % w/w |
| --- | --- |
| Potassium sorbate | 0.15 |
| Sodium Benzoate | 0.1 |
| Lactic acid/TEA 50% | q.s. pH |
| Sucralose solution 10% | 0.4 |
| Menthol | 0.7 |

Tests for the Removal and Inhibition of Bacterial Plaque.

16- to 24-year-old male and female patients who assisted the same educational establishment were voluntarily enrolled.

For all cases, tests were performed following the protocol described hereinafter.

Case 1

Remarks: patients with orthodontic appliances.

Treatment with Conventional Toothpaste, Days 1 to 30

The patient was instructed to follow a normal diet during treatment days and to clean his teeth after every meal during 30 days using a commercially conventional toothpaste and applying a quantity of paste that covers the entire brushing surface of the toothbrush. After a 10-minute brushing, a 20-second rinse with water was indicated.

Once the 30-day treatment with conventional toothpaste was completed, the patient was requested to attend a dentist appointment on day 30 when a blue plaque developer agent was applied and bacterial plaque build-up was observed on the surface of the teeth (FIG. 1).

Treatment with the Disclosed Composition, Days 31 to 60 and Days 61 to 90

The same patient was instructed to follow the same procedure previously described for case 1 during an additional 30-day term, but additionally applying a droplet of the disclosed gel composition as described in examples 1 or 2. (FIG. 2)

Once the treatment with the disclosed composition was completed, the patient was requested to attend a dentist appointment on day 60 when a blue plaque developer agent was applied and it was observed that bacterial plaque build-up was low or non-existent compared to the results obtained with the conventional toothpaste (FIG. 3).

The same procedure was repeated during an additional 30-day period comprising days 61 to 90; the patient was requested to attend a dentist appointment on day 90, when a blue plaque developer agent was applied and no bacterial plaque build-up was observed (FIG. 4).

Additional Remarks

The use of the disclosed composition facilitated the cleaning of brackets.

Less food accumulation was observed in the brackets.

Delayed adhesion of bacterial plaque was observed.

An agreeable breath was kept for a long period of time.

The healing of microinjuries caused by brackets was observed.

Case 2

Treatment with Conventional Toothpaste, Days 1 to 30

The patient was instructed to follow a normal diet during treatment days and to clean his teeth after every meal during 30 days using a commercially conventional toothpaste and applying a quantity of paste that covers the entire brushing surface of the toothbrush. After a 10-minute brushing, a 20-second rinse with water was indicated.

Figures 5, 6, 7:

Once the treatment with conventional toothpaste was completed, on day 30 a blue plaque developer agent was applied and bacterial plaque build-up was observed on the surface of the teeth (FIG. 5).

Treatment with the Composition Proposed, Days 31 to 60 and Days 61 to 90

The same patient was instructed to follow the same procedure previously described during an additional 30-day term, but additionally applying a droplet of the disclosed gel composition as described in examples 1 or 2.

Once the treatment with the disclosed composition was completed, the patient was requested to attend a dentist appointment on day 60 when a blue plaque developer agent was applied and it was observed that bacterial plaque build-up was low or non-existent compared to the results obtained with the conventional toothpaste (FIG. 6).

The same procedure was repeated during an additional period of time of 30 days, comprising days 61 to 90. Once the treatment with the disclosed composition was completed, the patient was requested to attend a dentist appointment on day 90 when a blue plaque developer agent was applied and no bacterial plaque build-up was observed. (FIG. 7).

Additional Remarks

Delayed adhesion of bacterial plaque was observed.

An agreeable breath was kept for a much longer period of time.

More brightness of the surface of teeth.

Case 3

Treatment with Conventional Toothpaste, Days 1 to 30

The patient was instructed to follow a normal diet during treatment days and to clean his teeth after every meal for 30 days using a commercially conventional toothpaste and applying a quantity of paste that covers the entire brushing surface of the toothbrush. After a 10-minute brushing, a 20-second rinse with water was indicated. (FIG. 9).

Figures 8, 9, 10:
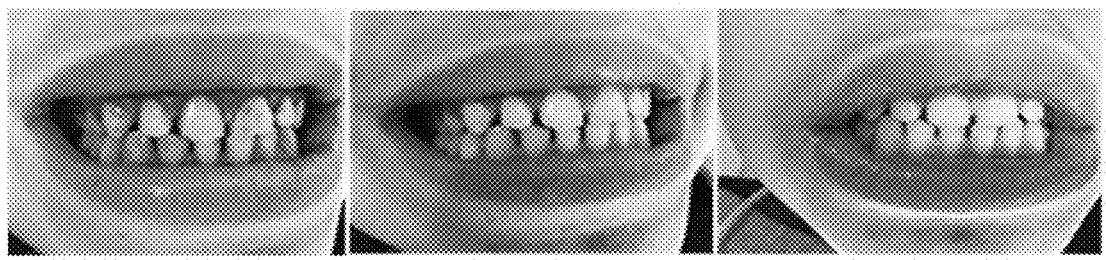

Once the treatment with conventional toothpaste was completed, the patient was requested to attend a dentist appointment on day 30; at that exact moment the blue plaque developer agent was applied and bacterial plaque build-up was observed on the surface of the teeth (FIG. 10).

Treatment with the Disclosed Composition, Days 31 to 60 and Days 61 to 90

The same patient was instructed to follow the same procedure previously described during an additional 30-day term, but additionally applying a droplet of the disclosed gel composition as described in examples 1 or 2. (FIG. 9)

Once the treatment with the disclosed composition was completed, on day 60 a blue plaque developer agent was applied and it was observed that bacterial plaque build-up was low or non-existent compared to the results obtained with the conventional toothpaste (FIG. 10).

Figures 11, 12, 13:
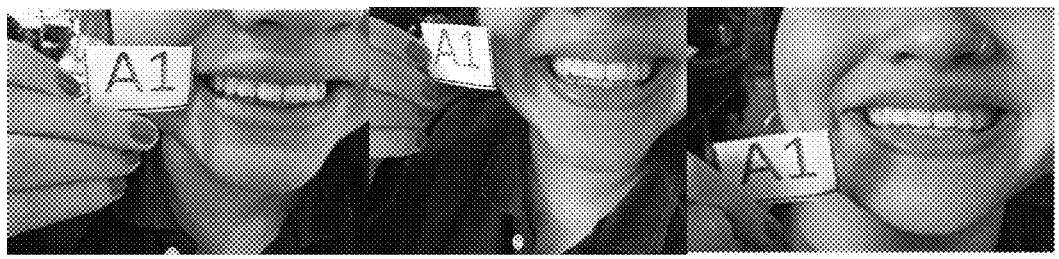

The same procedure was repeated during an additional period of time of 30 days, comprising days 61 to 90, and on day 90 the developer agent was applied (FIG. 11).

Additional Remarks

Delayed adhesion of bacterial plaque was observed.

An agreeable breath was kept for a much longer period of time.

The same procedures described in cases 1 to 3 were carried out in other 56 cases of 16- to 22-year-old female and male patients.

The images show the aspect of the teeth after the application of a red or blue bacterial plaque developer agent. The images clearly show that, after the treatment with the disclosed composition and by means of the application of a plaque developer agent on days 60 and 90, no bacterial plaque is detected, in contrast to the treatment with a conventional toothpaste, where bacterial plaque was detected in many cases.

TABLE 1

Figures 14, 15, 16:
Figures 17, 18, 19:
Figures 20, 21, 22:
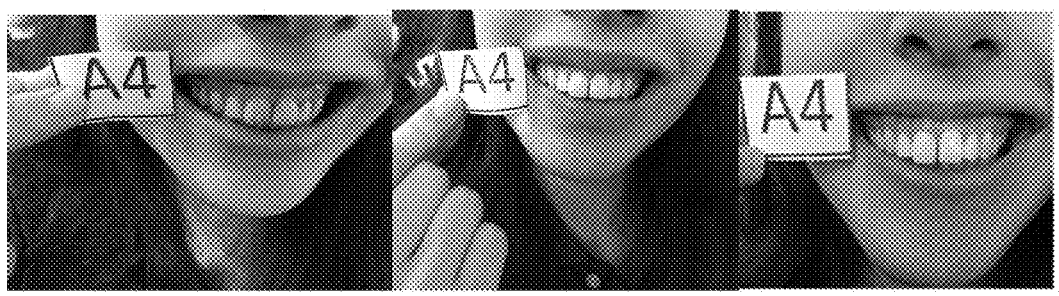
Figures 23, 24:
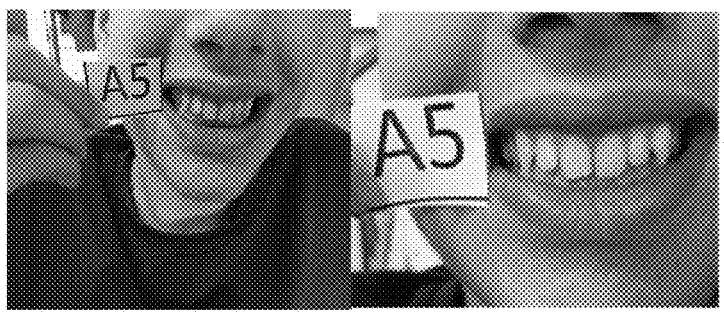
Figures 25, 26:
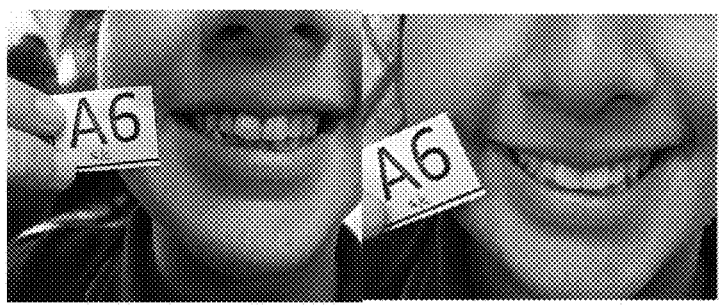
Figures 27, 28:
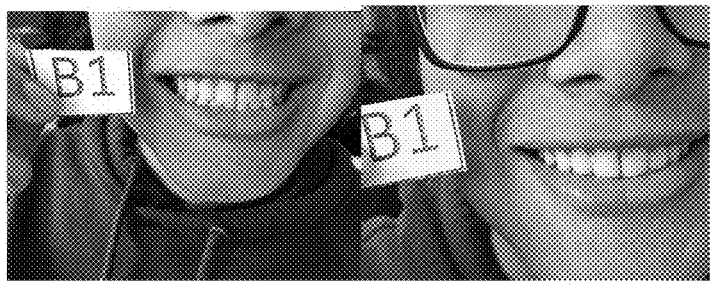
Figures 29, 30, 31:
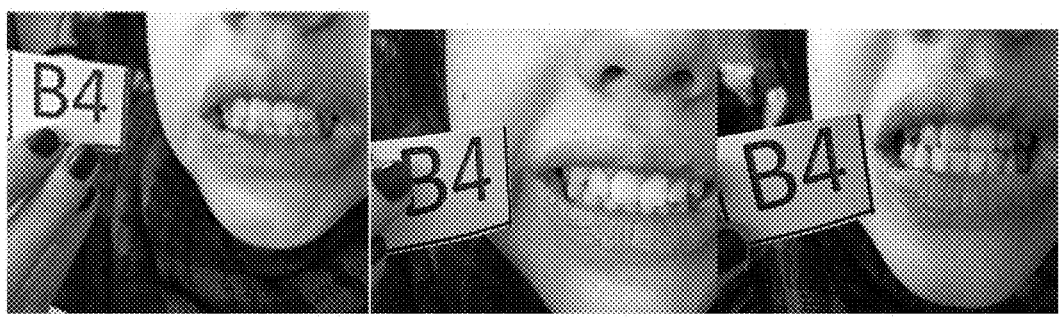
Figures 32, 33, 34:
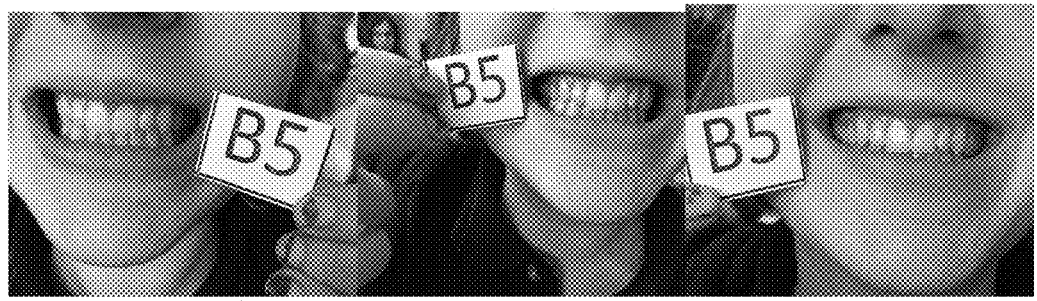
Figures 35, 36, 37:
Figures 38, 39:
Figures 40, 41:
Figures 42, 43, 44:
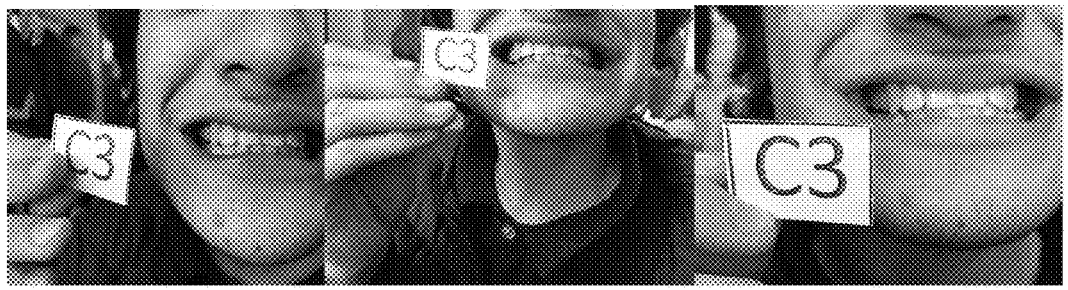
Figures 45, 46, 47:
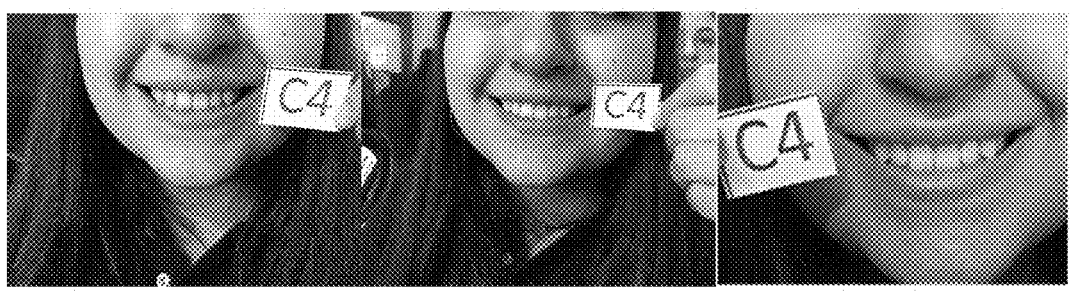
Figures 48, 49, 50:
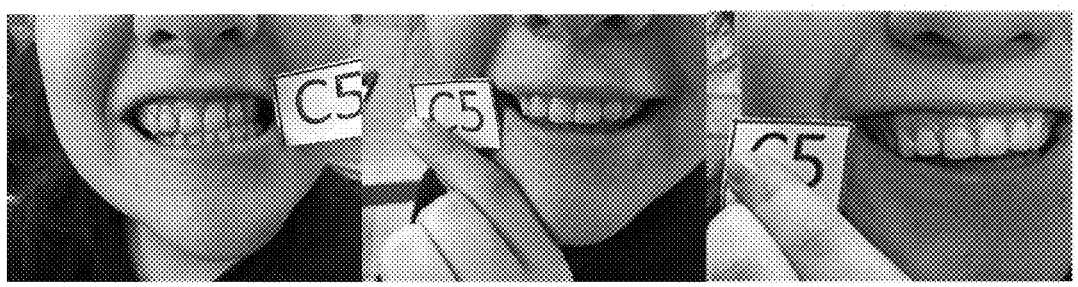
Figures 51, 52:
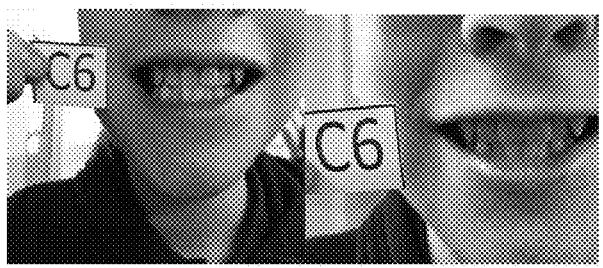
Figures 53, 54:
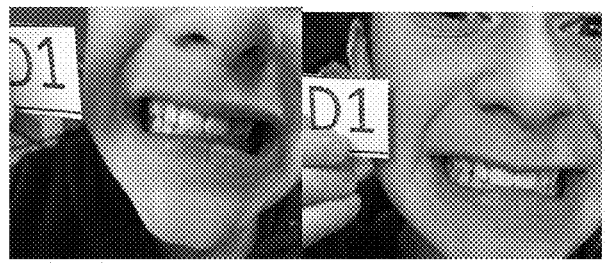
Figures 55, 56:
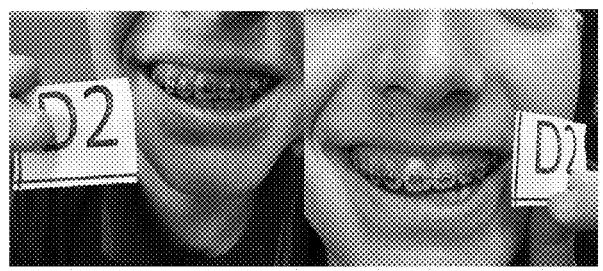
Figures 57, 58:
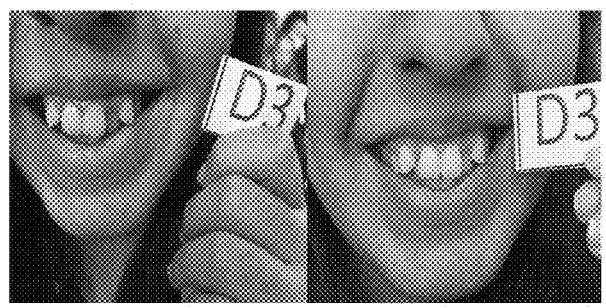
Figures 59, 60:
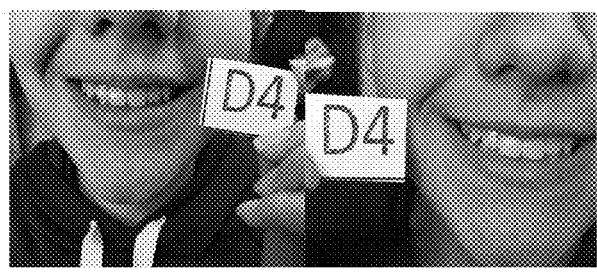
Figures 61, 62:
Figures 63, 64:
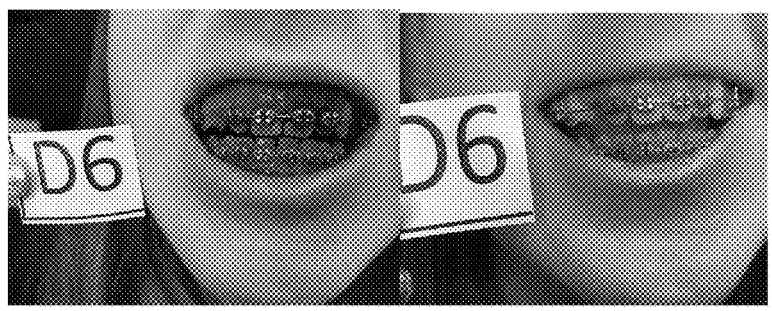

| CASE | Use of plaque developer agent on day 30 (conventional toothpaste) | Detection of bacterial plaque with developer agent | Use of disclosed plaque developer agent on day 60 | Detection of bacterial plaque with developer agent | Use of disclosed plaque developer agent on day 90 | Detection of bacterial plaque with developer agent |
|---|---|---|---|---|---|---|
| 1 | FIG. 1 | YES | FIG. 3 | NO | FIG. 4 | NO |
| 2 | FIG. 5 | YES | FIG. 6 | NO | FIG. 7 | NO |
| 3 | FIG. 8 | YES | FIG. 9 | NO | FIG. 10 | NO |
| A1 | FIG. 11 | YES | FIG. 12 | NO | FIG. 13 | NO |
| A2 | FIG. 14 | YES | FIG. 15 | NO | FIG. 16 | NO |
| A3 | FIG. 17 | YES | FIG. 18 | NO | FIG. 19 | NO |
| A4 | FIG. 20 | YES | FIG. 21 | NO | FIG. 22 | NO |
| A5 | FIG. 23 | YES | FIG. 24 | NO | (*) | (*) |
| A6 | FIG. 25 | YES | FIG. 26 | NO | (*) | (*) |
| B1 | FIG. 27 | YES | FIG. 28 | NO | (*) | (*) |
| B4 | FIG. 29 | YES | FIG. 30 | NO | FIG. 31 | NO |
| B5 | FIG. 32 | YES | FIG. 33 | NO | FIG. 34 | NO |
| B6 | FIG. 35 | YES | FIG. 36 | NO | FIG. 37 | NO |
| C1 | FIG. 38 | YES | FIG. 39 | NO | — | — |
| C2 | FIG. 40 | YES | FIG. 41 | NO | — | — |
| C3 | FIG. 42 | YES | FIG. 43 | NO | FIG. 44 | NO |
| C4 | FIG. 45 | YES | FIG. 46 | NO | FIG. 47 | NO |
| C5 | FIG. 48 | YES | FIG. 49 | NO | FIG. 50 | NO |
| C6 | FIG. 51 | YES | FIG. 52 | NO | (*) | (*) |
| D1 | FIG. 53 | YES | FIG. 54 | NO | (*) | (*) |
| D2 | FIG. 55 | YES | FIG. 56 | NO | (*) | (*) |
| D3 | FIG. 57 | YES | FIG. 58 | NO | (*) | (*) |
| D4 | FIG. 59 | YES | FIG. 60 | NO | (*) | (*) |
| D5 | FIG. 61 | YES | FIG. 62 | NO | (*) | (*) |
| D6 | FIG. 63 | YES | FIG. 64 | NO | (*) | (*) |
| D9 | FIG. 65 | YES | FIG. 66 | NO | (*) | (*) |

(*) the patient did not terminate the study

In all cases patients reported a freshener breath for a longer period of time as well as an immediate clean mouthfeel effect and an agreeable flavor, which was accomplished with the application of only one droplet of the product.

Each of the following terms written in singular grammatical form: "a", "an", and "the", as used herein, means "at least one", or "one or more". Use of the phrase One or more" herein does not alter this intended meaning of "a", "an", or "the". Accordingly, the terms "a", "an", and "the", as used herein, may also refer to, and encompass, a plurality of the stated entity or object, unless otherwise specifically defined or stated herein, or, unless the context clearly dictates otherwise. For example, the phrases: "a unit", "a device", "an assembly", "a mechanism", "a component, "an element", and "a step or procedure", as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: "includes", "including", "has", "having", "comprises", and "comprising", and, their linguistic/grammatical variants, derivatives, or/and conjugates, as used herein, means "including, but not limited to", and is to be taken as specifying the stated components), feature(s), characteristic(s), parameter(s), integer(s), or step(s), and does not preclude addition of one or more additional components), feature(s), characteristic(s), parameter(s), integer(s), step(s), or groups thereof. Each of these terms is considered equivalent in meaning to the phrase "consisting essentially of". Each of the phrases "consisting of and "consists of," as used herein, means "including and limited to".

The phrase "consisting essentially of," as used herein, means that the stated entity or item (system, system unit, system sub-unit device, assembly, sub-assembly, mechanism, structure, component element or, peripheral equipment utility, accessory, or material, method or process, step or procedure, sub-step or sub-procedure), which is an entirety or part of an exemplary embodiment of the disclosed invention, or/and which is used for implementing an exemplary embodiment of the disclosed invention, may include at least one additional feature or characteristic" being a system unit system sub-unit device, assembly, sub-assembly, mechanism, structure, component or element or, peripheral equipment utility, accessory, or material, step or procedure, sub-step or sub-procedure), but only if each such additional feature or characteristic" does not materially alter the basic novel and inventive characteristics or special technical features, of the claimed item.

The term "method", as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Throughout this disclosure, a numerical value of a parameter, feature, characteristic, object or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range "from 1 to 6" also refers to, and encompasses, all possible sub-ranges, such as "from 1 to 3", "from 1 to 4", "from 1 to 5", "from 2 to 4", "from 2 to 6", "from 3 to 6", etc., and individual numerical values, such as "1.3", "2", "2.8", "3", "3.5", "4", "4.6", "5", "5.2", and "6", within the stated or described numerical range of from 1 to 6". This applies regardless of the numerical breadth, extent or size, of the stated numerical range. Moreover, for stating or describing a numerical range, the phrase "in a range of between about a first numerical value and about a second numerical value", is considered equivalent to, and meaning the same as, the phrase "in a range of from about a first numerical value to about a second numerical value", and, thus, the two equivalents meaning phrases may be used interchangeably. For example, for stating or describing the numerical range of room temperature, the phrase "room temperature refers to a temperature in a range of between about 20° C. and about 25° C., and is considered equivalent to, and meaning the same as, the phrase "room temperature refers to a temperature in a range of from about 20° C. to about 25° C.

Terms of approximation, such as the terms about, substantially, approximately, etc., as used herein, refers to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment may also be illustratively described and presented in the context or format of a plurality of separate embodiments.

What is claimed is:

1. A coconut oil-based composition for oral and dental care and cleaning, characterized in that it comprises:
   25% to 45% w/w deionized water q.s.
   25% to 35% w/w coconut oil
   20% to 23% w/w first moisturizing agent,
   7% to 10% w/w second moisturizing agent,
   0.3% to 2.5% w/w structuring agent,
   0.15% to 0.3% w/w emulsifier/emollient,
   0.1% to 0.3% w/w gel thickener agent,
   0.05% to 0.15% w/w chelating agent,
   0.02% to 0.05% w/w conditioning agent,
   0% to 5% w/w pH-regulating agent,
   0% to 5% w/w alkalinizing agent,
   0.025% to 0.30% w/w of at least one preservative agent, and
   optionally, 0.5% to 2.5% of at least one flavoring.

2. A coconut oil-based composition for oral and dental care and cleaning according to claim 1, characterized in that said preservative agent is selected from the group that comprises at least one of imidazolidinyl urea, potassium sorbate; methylparaben; sodium benzoate, and propylparaben.

3. A composition for oral and dental care and cleaning according to claim 1, characterized in that the first moisturizing agent is glycerin.

4. A composition for oral and dental care and cleaning according to claim 1, characterized in that the second moisturizing agent is propylene glycol.

5. A composition for oral and dental care and cleaning according to claim 1, characterized in that the structuring agent is xanthan gum.

6. A composition for oral and dental care and cleaning according to claim 1, characterized in that the emulsifying/emollient agent is soybean lecithin.

7. A coconut oil-based composition for oral and dental care and cleaning according to claim 1, characterized in that the gel-forming thickener agent is a cetearyl alcohol and polyethylene glycol ether.

8. A composition for oral and dental care and cleaning according to claim 1, characterized in that the chelating agent is disodium EDTA.

9. A composition for oral and dental care and cleaning according to claim 1, characterized in that the conditioning agent is sucralose.

10. A composition for oral and dental care and cleaning according to claim 1, characterized in that the pH-regulating agent is triethanolamine.

11. A composition for oral and dental care and cleaning according to claim 1, characterized in that the acidity regulator agent is lactic acid.

12. A composition for oral and dental care and cleaning according to claim 2, characterized in that it comprises 0.2% to 0.3% w/w of imidazolidinyl urea; 0.05% to 0.15% w/w of potassium sorbate; 0.05% to 0.15% p/p of methylparaben; 0.05% to 0.15% w/w of sodium benzoate; 0.025% to 0.05% w/w of propylparaben.

13. A composition for oral and dental care and cleaning according to claim 1, comprising between:
   25% and 45% of deionized water,
   25% and 35% of coconut oil,
   20% and 23% of glycerin,
   7% and 10% of propylene glycol,
   0.3% and 2.5% of Xanthan gum,
   0.2% and 0.3% of imidazolidinyl urea,
   0.15% and 0.3% of soybean lecithin,
   0.05% and 0.15% of disodium EDTA,
   0.1% and 0.3% of a cetearyl alcohol and polyethylene glycol ether (Ceteareth 20)
   0.02% and 0.05% of sucralose,
   0% and 5% of TEA,
   0% and 5% of lactic acid,
   0.05% and 0.15% of potassium sorbate,
   0.05% and 0.15% of methylparaben,
   0.05% and 0.15% of sodium benzoate,
   0.025% and 0.05% of propylparaben.

14. A composition for oral and dental care and cleaning according to claim 1, characterized in that the coconut oil is incorporated to the composition in liquid state.

15. A composition for oral and dental care and cleaning according to claim 1, characterized in that it is in the form of a toothpaste.

16. A composition for oral and dental care and cleaning according to claim 1, characterized in that it is in the form of a gel.

17. A composition for oral and dental care and cleaning according to claim 1, characterized in that it is a cocoa-flavor gel composition that consists of the following ingredients in the quantities expressed in % w/w:

| Deionized water | q.s. 100 |
| --- | --- |
| Coconut Oil | 30 |
| Glycerin | 23 |
| Propylene Glycol | 10 |
| Xanthan Gum | 0.6 |
| Innidazolidinyl urea | 0.3 |
| Soybean Lecithin | 0.25 |
| Ceteareth 20 | 0.2 |
| Methylparaben | 0.1 |
| Disodiunn EDTA | 0.1 |
| Propylparaben | 0.05 |
| Potassium sorbate | 0.15 |
| Sodium Benzoate | 0.1 |
| Lactic acid | 0.73 |
| Sucralose solution 10% | 0.4 |
| Chocolate Flavor | 2.0 |

18. A composition for oral and dental care and cleaning according to claim 1, characterized in that it is a menthol-flavor gel composition that consists of the following ingredients in the quantities expressed in % w/w:

| Deionized water | q.s. 100 |
| --- | --- |
| Coconut Oil | 30 |
| Glycerin | 23 |
| Propylene Glycol | 10 |
| Xanthan Gum | 1.8 |
| Innidazolidinyl urea | 0.3 |
| Soybean Lecithin | 0.25 |
| Ceteareth 20 | 0.2 |
| Methylparaben | 0.1 |
| Disodiunn EDTA | 0.1 |
| Propylparaben | 0.05 |
| Potassium sorbate | 0.15 |
| Sodium Benzoate | 0.1 |
| Lactic acid/TEA 50% | q.s. pH |
| Sucralose solution 10% | 0.4 |
| Menthol | 0.7 |

* * * * *

UNITED STATES PATENT AND TRADEMARK OFFICE
CERTIFICATE OF CORRECTION

PATENT NO. : 10,610,481 B1
APPLICATION NO. : 16/429385
DATED : April 7, 2020
INVENTOR(S) : Ingrid Cristina Pellegrino Page 1 of 1

It is certified that error appears in the above-identified patent and that said Letters Patent is hereby corrected as shown below:

In the Claims

Column 10 Claim 17, Line 33 – please replace "Innidazolidinyl urea 0.3" with ---Imidazolidinyl urea 0.3---

Column 10 Claim 17, Line 37 – please replace "Disodiunn EDTA 0.1" with ---Disodium EDTA 0.1---

Column 10 Claim 18, Line 54 – please replace "Innidazolidinyl urea 0.3" with ---Imidazolidinyl urea 0.3---

Column 10 Claim 18, Line 58 – please replace "Disodiunn EDTA 0.1" with ---Disodium EDTA 0.1---

Signed and Sealed this
Ninth Day of June, 2020

Andrei Iancu
*Director of the United States Patent and Trademark Office*